United States Patent [19]

Portnyagina et al.

[11] 4,455,312
[45] Jun. 19, 1984

[54] 2-(O-CARBOXYPHENYLAMINO)-6H-PYRIMIDO(2,1-B)-QUINAZOLONE-6 AND DERIVATIVES THEREOF, AND APPLICATION AS ANTIPHLOGISTICS

[76] Inventors: Vera A. Portnyagina, ulitsa Bozhenko, 13, Kievo-Svyatoshinsky raion, Boyarka; Valentina K. Karp, ulitsa Shamrylo, 12-b, kv. 16, Kiev; Irina S. Barkova, ulitsa Pirogovskaya, 29, kv. 9, Kiev; Fedor P. Trinus, Brest-Litovsky prospekt, 12, kv. 13, Kiev; Nikolai A. Mokhort, ulitsa Serafimovicha, 6, kv. 77, Kiev; Alexandra G. Fadeicheva, ulitsa Karla Marxa, 9, kv. 29, Kiev; Galina I. Kozhushko, ulitsa Dobrokhotova, 5, kv. 72, Kiev; Tatyana K. Ryabukha, ulitsa Leiptsigskaya, 12, kv. 35, Kiev; Alexandr G. Panteleimonov, Kharkovskoe shosse, 12, kv. 47, Kiev; Viktor V. Kljushin, ulitsa Korostyshevskaya, 24, Kiev; Jury N. Dobrovolsky, ulitsa Geroev Dnepra, 26, kv. 95, Kiev; Larisa M. Kirichek, ulitsa Semashko, 12, kv. 89, Kiev; Adolf A. Medvedovsky, ulitsa Yanvarskogo Vosstania, 3, kv. 85, Kiev; Galina A. Getman, ulitsa Miljutenko, 10/1, kv. 147, Kiev; Jury D. Usenko, ulitsa Pushkinskaya, 13, kv. 54, Kiev; Viktor M. Sidelnikov, ulitsa Bogomoltsa, 11/12, kv. 12, Kiev; Nikolai F. Danilevsky, ulitsa Chekistov, 11/12, kv. 12, Kiev; Yakov P. Solsky, Bulvar Shevchenko, 35, kv. 12, Kiev, all of U.S.S.R.

[21] Appl. No.: 409,761

[22] Filed: Aug. 19, 1982

[51] Int. Cl.[3] ............... A61K 31/505; C07D 487/04
[52] U.S. Cl. .................................. 424/251; 544/250
[58] Field of Search ..................... 544/250; 424/251

[56] References Cited

U.S. PATENT DOCUMENTS

| | | | |
|---|---|---|---|
| 3,598,823 | 8/1971 | Hardtmann | 424/251 X |
| 3,969,506 | 7/1976 | Hardtmann | 424/251 |
| 4,083,980 | 4/1978 | Schromm et al. | 424/251 |

FOREIGN PATENT DOCUMENTS

| | | | |
|---|---|---|---|
| 77093 | 6/1977 | Japan | 424/251 |
| 953741 | 4/1964 | United Kingdom . | |

OTHER PUBLICATIONS

Journal of Pharmacology and Experimental Therapeutics, Dec. 1962, vol. 138, Number 3, pp. 405–413.
Yanai et al., Chemical Abstracts, vol. 55, 4515b, (1961).

*Primary Examiner*—Donald G. Daus
*Assistant Examiner*—Diana G. Rivers
*Attorney, Agent, or Firm*—Ladas & Parry

[57] ABSTRACT

2-(o-carboxyphenylamino)-6H-pyrimido(2,1-b)-quinazolone-6 has the structural formula

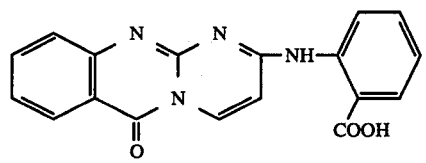

Derivatives thereof have the structural formulas

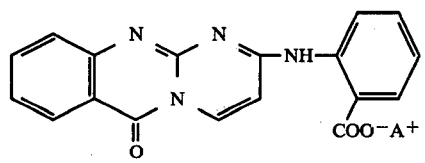

where $A^+$ are alkali metals, monoethanolamine, diethylamine.

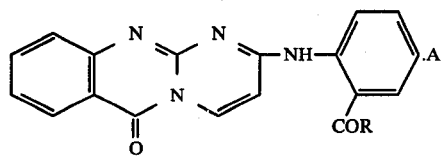

where R is OH, alkyloxyl C 1-4, $NHR^1$, where $R^1$ is H, alkyl C 1-4, phenyl, aralkyl. A are salts of inorganic acids

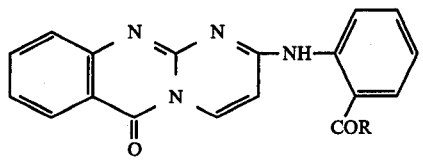

where R is alkyloxyl C 1-4, NHR', where R' is alkyl C 1-4.

A method of producing 2-(o-carboxyphenylamino)-6H-pyrimido(2,1-b)-quinazolone-6 and derivatives thereof consists in that 2,4-dichloropyrimidine is brought into interaction with anthranilic acid, or a sodium salt of anthranilic acid, or substituted esters, or amides of anthranilic acid in an aqueous medium, or in an organic solvent at a temperature of 90° to 120° C., is kept at this temperature for 1 to 4 hours, and an end product is separated using a conventional method.

A chemotherapeutic antiphlogistic, containing as an acting source 2-(o-carboxyphenylamino)-6H-pyrimido(2,1-b)-quinazolone-6 or derivatives thereof, and a pharmaceutical basic material.

12 Claims, No Drawings

2-(O-CARBOXYPHENYLAMINO)-6H-PYRIMIDO(2,1-B)-QUINAZOLONE-6 AND DERIVATIVES THEREOF, AND APPLICATION AS ANTIPHLOGISTICS

FIELD OF THE INVENTION

The invention deals with novel substances relating to pyrimidoquinazolones, and specifically to 2-(o-carboxyphenylamino)-6H-pyrimido(2,1-b)-quinazolone-6 and derivatives thereof, method of producing same and application as medicinals.

The invention can be utilized in the medical practice.

SUMMARY OF THE INVENTION

According to the invention, 2-(o-carboxyphenylamino)-6H-pyrimido(2,1-b)-quinazolone-6 has the following structural formula:

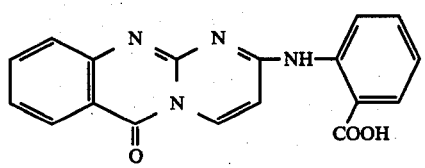

The above compound is a crystalline light yellow substance, soluble in alkaline solutions, and insoluble in water, alcohol, acetone, and chloroform. Its melting point is 290° C. (with decomposition).

Derivatives of 2-(o-carboxyphenylamino)-6H-pyrimido(2,1-b)-quinazolone-6 have the following structural formula:

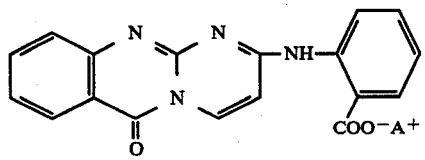

where $A^+$ are alkali metals, monoethanolamine, diethylamine.

Said compounds are colorless crystalline substances soluble in water and lower alcohols, and insoluble in ethers, chloroform, dimethyl formamide. Their melting point is 250° to 300° C. (with decomposition).

Still another group of derivatives of 2-(o-carboxyphenylamino)-6H-pyrimido(2,1-b)-quinazolone-6 have the following structural formula:

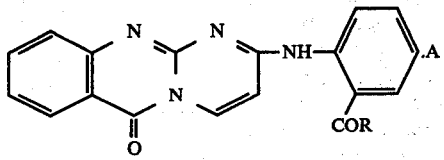

where
R is OH, alkyloxyl C 1–4,
$NHR^1$ where $R^1$ is H, alkyl C 1–4, phenyl, aralkyl,
A are salts of inorganic acids.

Other derivatives of 2-(o-carboxyphenylamino)-6H-pyrimido(2,1-b)-quinazolones-6 have the following structural formula:

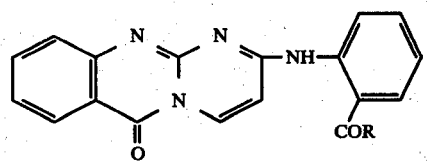

where R is alkyloxy C 1–4, $NHP^1$, where $P^1$ is alkyl C 1–4.

The above specified compounds are crystalline substances which are difficultly soluble in alcohols, dimethyl formamide, insoluble in water, acetone, and chloroform. Their melting point is 240° to 270° C. (with decomposition).

2-(o-carboxyphenylamino)-6H-pyrimido(2,1-b)-quinazolone-6 and derivatives thereof possess pharmacological activity and can be successfully used in medicine for the treatment of rheumatism and other diseases accompanied by an inflammatory process (arthritis, polyserositis, etc.).

The invention also consists in a method of producing 2-(o-carboxyphenylamino)-6H-pyrimido(2,1-b)-quinazolone-6 and derivatives thereof, wherein 2,4-dichloropyrimidine is brought into interaction with anthranilic acid, or a sodium salt of anthranilic acid, or substituted esters, or amides of anthranilic acid in an aqueous medium, or an inorganic solvent at a temperature of 90° to 120° C., held at this temperature for 2 to 4 hours, and an end product is separated using conventional methods.

The above method allows the above novel chemical substances to be produced at a high yield (70 to 80%). The method is technologically effective, does not require the application of complicated equipment and allows the products to be produced in one stage.

It is expedient to carry out interaction between the 2,4-dichloropyrimidine and a sodium salt of anthranilic acid in an aqueous medium having pH of 8.0 to 8.5.

The above modification of the method allows more soluble compounds to be produced in one stage.

It is most economic to conduct the interaction between 2,4-dichloropyrimidine and substituted esters or amides of anthranilic acid, with a ratio between the reactive substances being respectively 1:2, in an organic solvent.

It is possible to neutralize the amount of the acid product using conventional techniques.

Said modification of the method allows the range of produced products to be expanded.

To accelerate the process and to increase the yield of the end product, it is expedient to utilize alcohols, or dimethyl formamide, or acetic acid, or mixtures thereof as an organic solvent.

The invention also consists in the provision of a chemotherapeutic antiphlogistic, containing 2-(o-carboxyphenylamino)-6H-pyrimido(2,1-b)-quinazolone-6 or derivatives thereof and a pharmaceutical basic material as an active ingredient.

The above specified chemotherapeutic preparation is intented for treating patients suffering from rheumatoid arthritis, Bekhterev's disease, Reiter's disease, deforming asthenoarthrosis, chronic diseases of lungs and biliary tracts. This preparation can be used independently, as well as, in a mixture with other antiphlogistics (being of both steroid and nonsteroid nature).

One of modifications of the chemotherapeutic antiphlogistic is a preparation containing, as an acting source, 2-(o-carboxyphenylamino)-6H-pyrimido(2,1-b)-quinazolone-6 hydrochloride in an amount of 0.25 to 0.5 g, and a pharmaceutical basic material.

A pharmaceutically acceptable filler for tablets is used as as pharmaceutical base material. This filler may be sugar, milk sugar, starch, glucose, sodium hydrocarbonate, sodium chloride, disubstituted calcium phosphate, kaolin, dextrin, cacao, acetyl cellulose, methyl cellulose, polyvinyl alcohol, talc, calcium stearate, magnesium stearate, stearic acid, gelatin solution.

A modification of the chemotherapeutic antiphlogistic is a preparation containing, as an active ingredient, 2-(o-carboxyphenylamino)-6H-pyrimido(2,1-b)-quinazolone-6 hydrochloride and a pharmaceutical base material taken in the following ratio (percent by weight):

| | |
|---|---|
| 2-(o-carboxyphenylamino)-6H—pyrimido (2,1-b)-quinazolone-6 hydrochloride | 5 to 10 |
| pharmaceutical base material | 90 to 95 |

The pharmaceutical base material can be in the form of an ointment base, e.g. animal fats, fatty oils, lanolin, wax, spermaceti, fatty acids, higher alcohols, liquid paraffin, cellulose ethers, polysilicone compounds, phytosterols, bentonite clays.

Said ointments were used for external application in noninfectious burn lesions of skin regions.

Still another modification of the chemotherapeutic antiphlogistic is a preparation containing, as a pharmaceutical base material, a base for a paste.

The above specified preparation is expedient to be utilized in stomatology for treatment of various inflammatory diseases, particularly paradontosis. Clinical checking has demonstrated the efficiency of application of this preparation.

In addition, a modification of the chemotherapeutic antiphlogistic is a preparation containing, as an active ingredient, 2-(o-carboxyphenylamino)-6H-pyrimido(2,1-b)-quinazolone-6 hydrochloride in an amount of 0.1 to 0.5 g, and a pharmaceutical base material.

The pharmaceutical base material is a pharmaceutical filter for a suppository, e.g. cacao butter or a gelatinous-glyceric base.

DETAILED EXPLANATION OF THE INVENTION 2-(o-carboxyphenylamino)-6-H-pyrimido(2,1-b)-quinazolone-6 and its derivatives were tested for acute toxicity.

Acute toxicity was determined in white mice (18 to 25 g), rats (150 to 180 g), rabbits (2000 to 3000 g), and cats (2500 to 3200 g).

Acute toxicity of 2-(o-carboxyphenylamino)-6H-pyrimido(2,1-b)-quinazolone-6 and its derivatives was determined in intra-abdominal and peroral administration; for cats in peroral administration. The state of the animals was observed for 7 days. The statistical analysis of obtained data was carried out in accordance with the method of Litchfield, Wilcockson and Van der Waerden. The results are given in Table 1. For the purpose of comparison, the same table shows the data on acute toxicity of the prior art antiphlogistics.

TABLE 1

| Kind of animals | Way of administration | 2-(o-carboxyphenyl amino)-6H—pyrimido (2,1-b)-quinazolone-6 | 2-(o-carboxyphenyl-amino)-6H—pyrimido (2,1-b)-quinazolone-6 hydrochloride | Methyl ester of 2-(o-carboxyphenyl-amino)-6H—pyrimido (2,1-b)-quinazolone-6 | 2-(o-methyl-carbamide phenyl-amino)-6H—pyrimido (2,1-b)-quinazolone-6 | Mephenamine acid-N—(2,3-dimeth-ylphenyl) anthranilic acid | Phenyl butazone 1,2-diphenyl-4-butyl pyra-solidine-dion-3,5 | Method of determination |
|---|---|---|---|---|---|---|---|---|
| | | | | $LD_{50}$, mg/kg | | | | |
| Mice | Intra-abdominal | 1050 | 1050 | 1160 | 3000 | 150 | 250 | Litchfield and Wilcockson |
| | Peroral | 3400 | 3400 | — | — | — | — | Litchfield and Wilcockson |
| Rats | Intra-abdominal | 980 | 980 | — | — | 180 | 210 | Litchfield and Wilcockson |
| | Peroral | 3800 | 3800 | — | — | 520 | 720 | Litchfield and Wilcockson |
| Rabbits | Intra-abdominal | 1750 | 1750 | — | — | — | — | Van der Waerden |
| | Peroral | 5000 | 500 | — | — | — | — | |
| Cats | Peroral | 5000 | — | — | — | — | — | |

$LD_{50}$ means hereinafter ½ of a lethal dose.

Chronic toxicity of 2-(o-carboxyphenylamino)-6H-pyrimido(2,1-b)-quinazolone-6 and its derivatives was determined in rats and guinea pigs. The above substances were administered daily, once a day, perorally through a gastric tube in a conditionally therapeutic dose (100 mg/kg of mass) dissolved in 0.5 ml distilled water. Apricot gum, gum arabic, gelatose, starch, a serge-like fabric were used as an emulgator.

The results of investigations prove that 2-(o-carboxyphenylamino)-6H-pyrimido(2,1-b)-quinazolone-6 and its derivatives, when administered perorally in a selected dose (100 mg/kg), have not exerted appreciable effect for 10 days on the composition of peripheric blood in experimental animals. In the daily administration of said compound for 2 months, the results were obtained indicating the fact that general analysis of blood, differential blood count, and thrombocytes, which had been determined in dynamics during the whole experiment once a day, remained within the limits of physiological variations for the given kind of animal. This circumstance differentiates advantageously 2-(o-carboxyphenylamino)-6H-pyrimido(2,1-b)-quinazolone-6 and its derivatives from other nonsteriod antiphlogistics which, when being administered for a long time, adversely effect to a variable degree the composition of peripheric blood in patients.

To reveal the effect of 2-(o-carboxyphenylamino)-6H-pyrimido(2,1-b)-quinazolone-6 and its derivatives on the organism in prolonged administration, morphologic studies were conducted on the internal organs of experimental animals (rats), i.e. lungs, heart, liver, kidneys, adrenal glands, mucuos coats of stomach and intestine.

2-(o-carboxyphenylamino)-6H-pyrimido(2,1-b)-quinazolone-6 or its derivatives were administered daily, perorally through a gastric tube for 3 months in the above specified dose. The animals were killed after 5, 30, and 90 days. In total, during 3 months the animals received more than $3LD_{50}$. The tissues were fixed in formol and Carnois liquid. Paraffin and frozen sections were prepared. Histologic and histochemical of investigation were used.

In the thorough morphologic study of organs of animals which received 2-(o-carboxyphenylamino)-6H-pyrimido(2,1-b)-quinazolone-6 and its derivatives in a conditionally therapeutic dose for a long time, no pathologic changes were noticed as against the norm.

The antiinflammatory effect of 2-(o-carboxyphenylamino)-6H-pyrimido(2,1-b)-quinazolone-6 and its derivatives were evaluated from antiexudative and antiproliferative efficiency and from their influence on the formation of necrotic processes within the inflammation focus.

Antiexudative effect of 2-(o-carboxyphenylamino)-6H-pyrimido(2,1-b)-quinazolone-6 and its derivative were studied using a model of foot edema in a rat, caused by various phlogogenic stimuli (formalin, carrageenin, ovalbumin, serotonin, trypsin, and hyaluronidase).

The growth of foot endema in the rat was registered in dynamics after each hour from the moment of subplantar administration of a stimulus during 5 hours. Percentage of inhibition of the foor emeda in the rat was calculated from the following formula:

$$\text{percentage of inhibition} = \frac{V_k - V_o}{V_k} \cdot 100,$$

where $V_k$ is the volume of a control edematic foot minus the initial volume of the same foot prior to edema;

$V_o$ is the volume of the tested edematic foot minus the initial volume of the same foot prior to edema.

The development of the edema in the formalin inflammation was characterized by a moderate growth of the edema, the maximum magnitude of its acuteness being 3 to 4 hours after subplantar administration of a stimulus (2% solution of formalin, 0.1 ml to each foot). By this time, a classical local inflammation developed in the animals, said inflammation accompanied by the formation of an edema, hyperemia, and considerable painfulness. Inflammation of a foot was maintained for 7 and more days, and after 3 to 4 days necrosises are often formed in the place of injection of formalin.

Antiinflammatory effect of 2-(o-carboxyphenylamino)-6H-pyrimido-(2,1-b)-quinazolone-6 hydrochloride is given in Table 2 as against that of the prior art antiphlogistics.

TABLE 2

| Preparation 1 | Dose, mg/kg 2 | Way of administration 3 | Number of tests 4 | Percentage of inhibition 5 | Therapeutical index 6 |
|---|---|---|---|---|---|
| 2-(o-carboxyphenyl-amino)-6H—pyrimido (2,1-b)-quinazolone-6 | 5 | Intra-abdominal | 5 | 28 | 59.8 |
|  | 10 |  | 5 | 47 | 59.8 |
|  | 49 |  | 5 | 55 | 59.8 |
|  | 98 |  | 5 | 70 | 59.8 |
| 2-(o-carboxyphenyl-amino)-6H—pyrimido (2,1-b)-quinazolone-6 hydrochloride | 5 | Intra-abdominal | 5 | 31 | 61.2 |
|  | 10 |  | 5 | 50 | 61.2 |
|  | 49 |  | 5 | 57 | 61.2 |
|  | 98 |  | 5 | 71 | 61.2 |
| Mephenamine acid-N—(2,3-dimethyl phenyl) anthranilic acid | 9 | Intra-abdominal | 5 | 22 | 1.5 |
|  | 18 |  | 5 | 24 | 1.5 |
|  | 36 |  | 5 | 31 | 1.5 |
|  | 72 |  | 5 | 33 | 1.5 |
| Phenylbutazone-1,2-diphenyl-4-butyl pyrazolidone-dion-3,5 | 21 | Intra-abdominal | 5 | 17 | 2.8 |
|  | 42 |  | 5 | 40 | 2.8 |
|  | 82 |  | 5 | 51 | 2.8 |
| Sodium salicylate-6-oxybenzoic acid, sodium salt | 65 | Intra-abdominal | 5 | 14 | 1.8 |
|  | 130 |  | 5 | 24 | 1.8 |
|  | 260 |  | 5 | 41 | 1.8 |

Therapeutic index is hereinafter determined as $LD_{50}/ED_{50}$, where $ED_{50}$ is a dose allowing the effect to be achieved in 50% cases out of 100%.

The results obtained indicate that the development of a formalin edema of a foot in the rat was the most actively depressed by 2-(o-carboxyphenylamino)-6H-pyrimido(2,1-b)-quinazolone-6, and by 2-(o-carboxyphenylamino)-6H-pyrimido(2,1-b)-quinazolone-6 hydrochloride. The advantges of 2-(o-carboxyphenylamino)-6H-pyrimido(2,1-b)-quinazolone-6 and those of its derivative are also confirmed by pharmacotherapeutic width of effect (evaluated from therapeutic index).

Simultaneously with the inhibition of formalin edema, 2-(o-carboxyphenylamino)-6H-pyrimido(2,1-b)-quinazolone-6 and its derivative decreased other symptoms of inflammation, i.e. hyperemia and painfulness, and prevented subsequent formation of necrotic foci at the location of injection of formalin, which fact is almost noncharacteristic of mephenamine acid, butadiene and sodium salicylate.

Similar results have been obtained for other derivatives of 2-(o-carboxyphenylamino)6-H-pyrimido(2,1-b)-quinazolone-6.

Taking into account that nonsteroid antiphlogistics produce different influences on inflammatory edemas of various genesis, the action of 2-(o-carboxyphenylamino)-6H-pyrimido(2,1-b)-quinazolone-6 and its derivatives on other types of edemas were studied.

A carrageenin edema was induced by subplantar administration in rats of 0.1 ml 1% solution of carrageenin (polysaccharide prepared from Iceland or pearl moss).

In the control test, the edema grew quickly and reached the maximum magnitude (201%) after 3 to 4 hours following the injection of carrageenin. Table 3 gives the data on the inflammatory action of 2-(o-carboxyphenylamino)-6H-pyrimido(2,1-b)-quinazolone-6, and 2-(o-carboxyphenylamino)-6H-pyrimido(2,1-b)-quinazolone-6 hydrochloride. For the purpose of comparison, this table also gives the data on the inflammatory action of the prior art antiphlogistics.

TABLE 3

| Preparation | Dose, mg/kg | Way of administration | Number of tests | Percentage of inhibition | Therapeutical index |
|---|---|---|---|---|---|
| 2-(o-carboxyphenyl-amino)-6H—pyrimido(2,1-b)-quinazolone-6 | 25<br>49<br>98 | Intra-abdominal | 5<br>5<br>5 | 11<br>25<br>54 | 9.8 |
| 2-(o-carboxyphenyl-amino)-6H—pyrimido(2,1-b)-quinazolone-6 hydrochloride | 25<br>49<br>98 | Intra-abdominal | 5<br>5<br>5 | 12<br>26<br>55 | 10.9 |
| Mephenamine acid-N—(2,3-dimethyl phenyl) anthranilic acid | 25<br>50<br>100 | Intra-abdominal | 5<br>5<br>5 | 33<br>44<br>50 | 1.8 |
| Phenylbutazone-1,2-diphenyl-4-butyl pyrazolidine-dion-3,5 | 21<br>42<br>84 | Intra-abdominal | 5<br>5<br>5 | 27<br>44<br>51 | 3.5 |
| Sodium salicylate-6-oxybenzoic acid, sodium salt | 65<br>90<br>130 | Intra-abdominal | 5<br>5<br>5 | 14<br>32<br>56 | 5.6 |

It follows from the above Table that 2-(o-carboxyphenylamino)-6H-pyrimido(2,1-b)-quinazoline-6 and its derivative possess a higher antiinflammatory activity.

An ovalbumin edema was induced by subplantar administration in rats of egg albumin (0.1 ml per foot). The edema developed very intensely, i.e. reached the maximum magnitude (191%) as soon as 1 hour following the injection of ovalbumin, and completely disappeared by the end of the day.

The preparations under studies were administered in the given investigations in a dose corresponding to 1/10LD$_{50}$ for the rats in the intra-abdominal administration.

Antiexudative effect of 2-(o-carboxyphenylamino)-6H-pyrimido(2,1-b)-quinasolone-6 and its derivatives with the given type of edema corresponds to the level of mephenamine acid and sodium salicylate. At the moment of maximum development of an ovalbumin edema (1 to 2 hours after injection of ovalbumin), its manifestation was inhibited by 27 to 30%. During subsequent hours, the antiinflammatory effect of 2-(o-carboxyphenylamino)6H-pyrimido(2,1-b)-quinazolone-6 and its derivatives of mephenamine acid and sodium salicylate increased. With the given kind of aseptic inflammation, phenylbutazone did not produce antiedematic effect.

Antiproliferative properties of 2-(o-carboxyphenylamino)-6H-pyrimido(2,1-b)-quinazolone-6 and its derivatives have been studied as compared with other nonsteroid preparations in the experiments with "cotton granuloma".

The term "cotton granuloma" means hereinafter the formation of a granular-fibrous tissue around cotton balls implanted into experimental animals.

The influence of these nonsteroid antiinflammatory preparations on the formation of a "cotton granuloma" is shown in Table 4.

TABLE 4

| Preparation | Dose, mg/kg | Number of tests | Percentage of inhibition | Therapeutical index |
|---|---|---|---|---|
| 2-(o-carboxyphenylamino)-6H—pyrimido(2,1-b)-quinazolone-6 | 48<br>95<br>190 | 5<br>9<br>7 | 17<br>25<br>50 | 20.5 |
| 2-(o-carboxyphenylamino)-6H—pyrimido(2,1-b)-quinazolone-6 hydrochloride | 48<br>95<br>190 | 5<br>9<br>7 | 18<br>24<br>52 | 22.3 |
| Mephenamine acid-N—(2,3-dimethyl phenyl) anthranilic acid | 13<br>52<br>78 | 9<br>7<br>5 | 33<br>42<br>52 | 7.43 |
| Phenylbutazone-1,2-diphenyl-4-butyl pyrazolidine-dion-3,5 | 18<br>72<br>108 | 10<br>7<br>5 | 6<br>44<br>58 | 8.27 |
| Sodium salicylate-6-oxybenzoic acid, sodium salt | 60<br>80<br>160<br>240 | 8<br>20<br>36<br>52 | 8<br>20<br>36<br>52 | 7.27 |

As can be seen from the above data, the most effective among the given preparations were those of 2-(o-carboxyphenylamino)-6H-pyrimido(2,1-b)-quinazolone-6, 2-(o-carboxyphenylamino)-6H-pyrimido(2,1-b)-quinazolone-6 hydrochloride, and mephenamine acid.

At the same time, pharmacotherapeutic width of effect of 2-(o-carboxyphenylamino)-6H-pyrimido(2,1-b)-quinazolone-6 and its derivative 2-(o-carboxyphenylamino)-6H-pyrimido(2,1-b)-quinazolone-6 hydrochloride is three times that of mephenamine acid, sodium salicylate, and phenylbutazone. The inhibition of proliferative processes of other derivative of 2-(o-carboxyphenylamino)-6H-pyrimido(2,1-b)-quinazolone-6 is at the level of inhibition of 2-(o-carboxyphenylamino)6H-pyrimido(2,1-b)-quinazolone-6 hydrochloride.

The analgetic activity of 2-(o-carboxyphenylamino)-6H-pyrimido(2,1-b)-quinazolone-6 and its derivatives was judged from the variation of the threshold of pain sensitivity in the contact-heat stimulation.

Table 5 gives the data on the analgetic activity of 2-(o-carboxyphenylamino)-6H-pyrimido(2,1-b)-quinazolone-6 and its derivative 2-(o-carboxyphenylamino)-6H-pyrimido(2,1-b)-quinazolone-6 hydrochloride in the contact-heat stimulation. For the purpose of comparison, this table also gives the data on the analgetic activity of the prior art antiphlogistics.

TABLE 5

| Preparation | Dose, mg/kg | Number of tests | Increase in latent period of pain reaction in mice, % | Therapeutical index |
|---|---|---|---|---|
| 2-(o-carboxyphenylamino)-6H—pyrimido(2,1-b)-quinazolone-6 | 52<br>105<br>157 | 7<br>10<br>8 | 30<br>51<br>60 | 10.8 |
| 2-(o-carboxyphenylamino)-6H—pyrimido(2,1-b)-quinazolone-6 hydrochloride | 52<br>105<br>157 | 7<br>10<br>8 | 31<br>52<br>62 | 11.0 |
| Mephenamine acid-N—(2,3-dimethyl phenyl) anthranilic acid | 3.5<br>7.0<br>15 | 9<br>8<br>9 | 18<br>36<br>43 | 8.3 |
| Phenylbutazone-1,2-diphenyl-4-butyl pyrazolidine-dion-3,5 | 25<br>50<br>100 | 6<br>7<br>9 | 8<br>43<br>92 | 4.7 |
| Sodium salicylate-6-oxybenzoic acid, sodium salt | 32<br>65<br>130 | 8<br>8<br>7 | 28<br>38<br>59 | 5.9 |

It follows from Table 5 that in the contact-heat stimulation, mephenamine acid possessed the most expressed analgetic effect. The analgetic activity of 2-(o-carboxyphenylamino)-6H-pyrimido(2,1-b)-quinazolone-6 and its derivative was considerably lower in this kind of stimulation than that of mephenamine acid and phenylbutazone, and is higher than that of sodium salicylate. However, 2-(o-carboxyphenylamino)-6H-pyrimido(2,1-b)-quinazolone-6 and its derivatives have greatest width of analgetic activity. Similar results have been obtained in other derivatives of 2-(o-carboxyphenylamino)-6H-pyrimido(2,1-b)-quinazolone-6. Antipyretic effect of 2-(o-carboxyphenylamino)-6H-pyrimido(2,1-b)-quinazolone-6 and its derivatives were investigated in rats suffering from pyrogenal fever. Maximum decrease in the temperature (degrees) was determined. In all the tests, 2-(o-carboxyphenylamino)-6H-pyrimido(2,1-b)-quinazolone-6 was used in a dose constituting 5% of $LD_{50}$, while the other preparations were used in a dose constituting 70% of $LD_{50}$.

Table 6 gives the data of antipyretic effect of 2-(o-carboxyphenylamino)-6H-pyrimido(2,1-b)-quinazolone-6 and its derivative. For the purpose of comparison, this table also gives the data on antipyretic effect of the prior art antiphlogistics.

TABLE 6

| Preparation | Antipyretic effect (maximum decrease in temperature), °C. |
|---|---|
| 2-(o-carboxyphenylamino)-6H—pyrimido (2,1-b)-quinazolone-6 | 1.4 |
| 2-(o-carboxyphenylamino)-6H—pyrimido (2,1-b)-quinazolone-6 hydrochloride | 1.4 |
| Indomethacin 1-(para-chlorobenzoyl)5-methoxy-2-methyl-indole-3-acetic acid | 0.7 |
| Bruphen-2-(para-isobutyl phenyl)-propionic acid | 1.3 |
| Mephenamine acid-N—(2,3-dimethyl phenyl) anthranilic acid | 1.2 |

According to the obtained data, antipyretic activity of 2-(o-carboxyphenylamino)-6H-pyrimido(2,1-b)-quinazolone-6 and its derivative is at the level of such preparations as bruphen and mephenamine acid, and considerably exceeds that of indomethacin.

Extensive clinical studies of the preparation made in the form of tablets containing 2-(o-carboxyphenylamino)-6H-pyrimido(2,1-b)-quinazolone-6 hydrochloride have been conducted. More than 400 patients of different ages were observed, suffering from active rheumatism, rheumatoid arthritis, Bekhterev's disease, Reiter's disease, deforming asthenoarthrosis, chronic diseases of lungs and biliary tracts.

The preparation was used in a daily dose of from 1.5-3.0 to 5.0 g. The duration of the treatment course was from two weeks to three months. Subjective improvement was observed by the 2nd-4th day, while objective improvement was registered after 7 to 10 days from the beginning of the treatment.

The chemotherapeutic preparation in the form of a paste was applied in stomatology for the treatment of paradontosis.

The method of treatment with the utilization of a paste containing 2-(o-carboxyphenylamino-6H-pyrimido(2,1-b)-quinazolone-6 hydrochloride as an acting source consisted in the following:

Pathologic tooth-gingival pockets were washed with a solution of antiseptics (nitrofurazone, rivanol) with subsequent introduction of the inventive paste into said pockets. To prolong the curvative effect, the introduced paste was covered with a hardenable bandage.

The course of treatment, depending on the passage and degree of development of a dystrophic-inflammatory form of paradontosis, included 3 to 10 sessions conducted daily or every other day.

The above specified method of treatment is simple and can be conducted both in a hospital or under ambulatory conductions. 175 patients were subjected to the treatment of paradontosis with the use of said paste, the treatment being successful in all the cases.

A positive effect was also obtained in the case of utilization of said chemotherapeutical preparation having an ointment base and a base for suppository.

The invention is further explained in terms of specific examples of embodiments thereof.

EXAMPLE 1

Anthranilic acid in an amount of 27.4 g was dissolved in 200 ml of 1h solution of sodium hydroxide. To this solution was added 2,4-dichloropyrimidine in an amount of 14.9 g, following which the resulting mixture was heated with stirring to a temperature of 100° C. The reaction mass was held at this temperature for 3 hours, cooled, and the formed precipitate of 2-(o-carboxyphenylamino)-6H-pyrimido(2,1-b)-quinazolone-6 was filtered. The precipitate thus obtained was purified by recrystallization from dimethyl sulfoxide, acetic acid, or reprecipitated from an alkali solution using an acid. The melting point of the precipitate was 290° C. (with decomposition). The yield of the end product was 75%.

EXAMPLE 2

Anthranilic acid in an amount of 27.4 g was dissolved in 200 ml of 1h solution of sodium hydroxide. The resulting solution was heated to a temperature of 90° C., and a solution of 14.9 g 2,4-dichloropyrimidine in 50 ml dimethyl formamide was added thereto gently with stirring. Following this, the temperature was raised to 100° C., and the resulting mixture was held for 2 hours. A precipitate thus formed of 2-(o-carboxyphenylamino)-6H-pyrimido(2,1-b)-quinazolone-6 was filtered, after cooling, and treated similarly to the method described in Example 1.

EXAMPLE 3

To a solution of 27.4 g anthranilic acid in 200 ml of 1h solution of sodium hydroxide heated to a temperature of 90° C., was added a solution of 14.9 g 2,4-dichloropyrimidine in 50 ml alcohol. The reaction mixture was stirred at a temperature of 100° C. and held for 4 hours. Then the mixture was treated as specified in Example 1.

EXAMPLE 4

Anthranilic acid in an amount of 3.0 g was dissolved in 300 ml of 0.1h solution of sodium hydroxide. To this solution was added 2,4-dichloropyrimidine in an amount of 1.5 g, and the resulting mixture was heated to a temperature of 100° C. and held with stirring for 2 hours. Then 200 ml of the solution were evaporated, a precipitate of a sodium salt of 2-(o-carboxyphenylamino)-6H-pyrimido(2,1-b)(quinazolone-6, which precipitated after cooling, was filtered, and purified by recrystallization from alcohol.

EXAMPLE 5

2-(o-carboxyphenylamino)-6H-pyrimido(2,1-b)-quinazolone-6 in an amount of 3.32 g (EXAMPLE 1) was added to a solution of 0.4 g sodium hydroxide in 50 ml absolute alcohol. The resulting mixture was left for dissolution, following which a sodium salt of 2-(o-carboxyphenylamino)-6-H-pyrimido(2,1-b)-quinazolone-6 was separated by adding 200 ml. ether to the solution, and purified by recrystallization from alcohol.

EXAMPLE 6

To a suspension of 3.32 g 2-(o-carboxyphenylamino)-6H-pyrimido(2,1-b)-quinazolone-6 in 10 ml alcohol was added with stirring 0.65 g. 2-aminoethanol. First, the starting substances were dissolved, following which a novel precipitate formed, said precipitate being an ethanol ammonium salt of 2-(o-carboxyphenylamino)-6H-pyrimido(2,1-b)-quinazolone-6, a crystalline substance soluble in water. The melting point of this substance was 255° C. (with decomposition). The yield of the end product was 80%.

EXAMPLE 7

2-(o-carboxyphenylamino)-6H-pyrimido(2,1-b)(quinazolone-6 in an amount of 3.32 g was mixed with 10 ml alcohol, and diethyl amine in an amount of 0.75 g was added thereto. The resulting solution of diethyl ammonium salt of 2-(o-carboxylphenylamino)6H-pyrimido(2,1-b)quinazolone-6 was treated as specified in Example 6. The melting point of this substance was 270° C. (with decomposition). The yield of the end product was 82%.

EXAMPLE 8

Anthranilic acid in an amount of 27.5 g and 14.9 g 2,4-dichloropyrimidine dissolved in 200 ml acetic acid were heated with stirring to a temperature of 105° C. and held at this temperature for 3 hours. A precipitate thus formed was filtered after cooling, washed with alcohol and ether. The resulting substance was 2-(o-carboxyphenylamino)6H-pyrimido(2,1-b)-quinazolone-6 hydrochloride, a crystalline substance having the melting point of 285° to 187° C. (with decomposition). The yield of the end product was 80%.

EXAMPLE 9

2,4-dichloropyrimide in an amount of 14.9 g and 30.2 g methyl ether of anthranilic acid were dissolved in 100 ml butanol. The mixture was heated at a temperature of 120° C. and held for 4 hours. Following this, the mixture was cooled, the formed precipitate was filtered, washed with acetone and then with ether. Methyl ester of 2-(o-carboxyphenylamino)-6H-pyrimido(2,1-b)-quinazolone-6 hydrochloride was recrystallized from methanol. The melting point was of 254° to 255° C. (with decomposition). The yield of the end product was 70%.

EXAMPLE 10

Ethyl ester of 2-(o-carboxylphenylamino)-6H-pyrimido(2,1-b)-quinazolone-6 hydrochloride was prepared from 14.9 g of 2,4-dichloropyrimidine and 33 g of ethyl ester of anthranilic acid using the method specified in Example 9. The melting point was of 242° to 244° C. (with decomposition). The yield of the end product was 67%.

EXAMPLE 11

The hydrochloride of the propyl ester of 2-(o-carboxylphenylamino)-6H-pyrimido(2,1-b)-quinazolone-6 was prepared from 14.9 g of dichloropyrimidine and 35.8 g of the propyl ester of anthranilic acid similarly to the method specified in Example 9. The melting point was of 233° to 235° C. (with decomposition). The yield of the end product was 67%.

EXAMPLE 12

The hydrochloride of the isopropyl ester of 2-(o-carboxyphenylamino)-6H-pyrimido(2,1-b)-quinazolone-6 was prepared similar to the method specified in Example 11. The melting point was of 241° to 242° C. (with decomposition). The yield of the end product was 65%.

EXAMPLE 13

The hydrochloride of the butyl ester of 2-(o-carboxyphenylamino)-6H-pyrimido(2,1-b)-quinazolone-6 was prepared from 14.9 g of 2,4-dichloropyrimidine and 38.6 g of the butyl ester of anthranilic acid using the method described above (Example 9). The melting point was of 243° to 245° C. (with decomposition). The yield of the end product was 71%.

EXAMPLE 14

2,4-dichloropyrimidine in an amount of 7.45 g and 13.6 g of o-aminobenzamide were dissolved in 50 ml of dimethyl formamide, and the resulting solution was heated to a temperature of 100° C. After 15 minutes, a precipitate of 2-(o-carboxyphenylamino)-6H-pyrimido(2,1-b)-quinazolone-6 began to form. Said mixture was held at a temperature of 100° C. for one more hour, following which the reaction mass was cooled to the room temperature, the precipitate was filtered, washed with dimethyl formamide, and then with ether. The melting point was of 241° to 242° C. (with decomposition). The yield of the end product was 80%.

EXAMPLE 15

The hydrochloride of 2-(o-methylcarbamide phenylamino)-6H-pyrimido(2,1-b)-quinazolone-6 was prepared from 7.45 g of 2,4-dichloropyrimidine and 15.0 g of o-methyl aminobenzamide according to the method specified in Example 14. The melting point was of 252° to 253° C. (with decomposition). The yield of the end product was 90%.

EXAMPLE 16

The hydrochloride of 2-(o-phenylcarbamide phenylamino)-6H-pyrimido(2,1-b)-quinazolone-6 was prepared from 7.45 g of 2,4-dichloropyrimidine and 21.2 g of phenyl amide of anthranilic acid similarly to the method described in Example 14. The melting point was of 257° C. (with decomposition). The yield of the end product was 60%.

EXAMPLE 17

The hydrochloride of 2-(o-benzylcarbamide phenylamino)-6H-pyrimido(2,1-b)-quinazolone-6 was formed in the interaction between 7.45 g of 2,4-dichloropyrimidine and 22.6 g of benzylamide of anthranilic acid using the method specified in Example 14. The melting point was of 254° to 255° C. (with decomposition). The yield of the end product was 76%.

EXAMPLE 18

The hydrochloride of 2-(o-carboxyphenylamino)-6H-pyrimido(2,1-b)-quinazolone-6 in an amount of 3.7 g was added to 50 ml of 0.2h solution of sodium hydroxide, agitated for 5 to 10 minutes, and filtered. The precipitate left on the filter was washed with water until the filtrate was free from chlorides. The melting point was 290° C. (with decomposition). The yield of the end product was 95%.

While particular embodiments of the invention have been shown and described, various modifications thereof will be apparent to those skilled in the art and therefore it is not intended that the invention be limited to the disclosed embodiments or to the details thereof and the departures may be made therefrom within the spirit and scope of the invention as defined in the claims.

We claim:

1. 2-(o-carboxyphenylamino)-6H-pyrimido(2,1-b)-quinazolone-6, having the structural formula

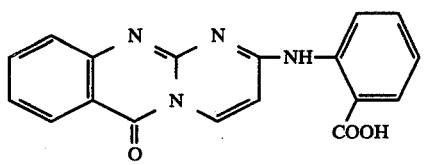

2. Derivatives of 2-(o-carboxyphenylamino)-6H-pyrimido(2,1-b)-quinazolone-6, having the structural formula

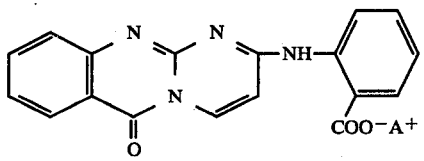

where A+ is selected from a group consisting of alkali metals, monoethanolamine, diethylamine.

3. Derivatives of 2-(o-carboxyphenylamino)-6H-pyrimido(2,1-b)-quinazolone-6, having the structural formula

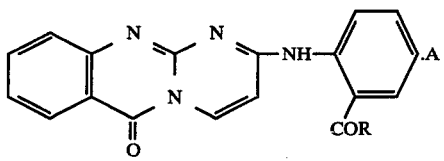

where R is OH, alkyloxyl $C_{1-4}$, $NHR^1$, where $R^1$ is H, alkyl $C_{1-4}$; phenyl-alkyloxy, aralkyl. A are salts of inorganic acids.

4. Derivatives of 2-(o-carboxyphenylamino)-6H-pyrimido(2,1-b)-quinazolone-6, having the structural formula

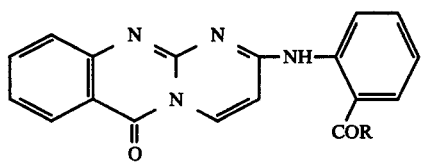

where R is alkyloxyl $C_{1-4}$, $NHR^1$, where $R^1$ is alkyl $C_{1-4}$.

5. A chemotherapeutic antiphlogistic containing, as an active ingredient, a substance selected from the group consisting of 2-(o-carboxyphenylamino)-6H-pyrimido(2,1-b)-quinazolone-6, derivatives of 2-(o-carboxyphenylamino)-6H-pyrimido(2,1-b)-quinazolone-6, and a pharmaceutical base material.

6. A chemotherapeutic antiphlogistic as set forth in claim 5, wherein it contains, as an active ingredient, 2-(o-carboxyphenylamino)-6-H-pyrimido(2,1-b)-quinazolone-6 hydrochloride in an amount of 0.25 to 0.5 g, and a pharmaceutical base material.

7. A chemotherapeutic antiphlogistic as set forth in claim 6, wherein it contains, as said pharmaceutical base material, a pharmaceutically acceptable filler for tablets.

8. A chemotherapeutic antiphlogistic as set forth in claim 5, containing as an active ingredient said 2-(o-carboxyphenylamino)-6H-pyrimido(2,1-b)-quinazolone-6 hydrochloride and said pharmaceutical basic material, the ratio between ingredients being the following (percent by weight):

| | |
|---|---|
| 2-(o-carboxyphenylamino)-6H—pyrimido (2,1-b)-quinazolone-6 hydrochloride | 5 to 10 |
| pharmaceutical base material | 90 to 95. |

9. A chemotherapeutic antiphlogistic as set forth in claim 8, containing a pharmaceutical base material being an ointment base.

10. A chemotherapeutic antiphlogistic as set forth in claim 8, containing a pharmaceutical base material being a base for a paste.

11. A chemotherapeutic antiphlogistic as set forth in claim 8, containing, as an acting source, 2-(o-carboxyphenylamino)-6H-pyrimido(2,1-b)-quinazolone-6 hydrochloride in an amount of 0.1 to 0.5 g, and a pharmaceutical base material.

12. A chemotherapeutic antiphlogistic as set forth in claim 11, containing a pharmaceutical filler for suppositories as a pharmaceutical base material.

* * * * *